US00PP14328P29

(12) United States Plant Patent
Plate

(10) Patent No.: US PP14,328 P2
(45) Date of Patent: Dec. 2, 2003

(54) PHALAENOPSIS PLANT NAMED 'EXOTIC MOON'

(50) Latin Name: *Phalaenopsis sp. Orchid*
Varietal Denomination: Exotic Moon

(76) Inventor: Renate Plate, Butendieker Landstr. 49A, D-28357 Bremen (DE)

( * ) Notice: Subject to any disclaimer, the term of this patent is extended or adjusted under 35 U.S.C. 154(b) by 4 days.

(21) Appl. No.: 10/232,896

(22) Filed: Aug. 31, 2002

(51) Int. Cl.[7] ..... A01H 5/00
(52) U.S. Cl. ..... Plt./311
(58) Field of Search ..... Plt./311

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Phalaenopsis plant named 'Exotic Moon', characterized by its yellow green-colored flowers with red purple-colored labellum; freely flowering habit; upright, freely branching and sturdy flowering stems, and excellent postproduction longevity.

2 Drawing Sheets

Botanical classification/cultivar designation: Phalaenopsis Orchid cultivar Exotic Moon.

BACKGROUND OF THE INVENTION

The present invention comprises a new and distinct cultivar of Phalaenopsis Orchid, and hereinafter referred to by the cultivar name, Exotic Moon.

The new cultivar is a product of a planned breeding program conducted by the Inventor in Bremen, Germany. The objective of the breeding program is to create new uniform pot-type Phalaenopsis Orchid cultivars having attractive flower coloration.

The new cultivar was discovered by the Inventor from within the progeny of a cross-pollination of two unidentified proprietary selections of Phalaenopsis Orchids, not patented, on Jul. 15, 1998, in a controlled environment in Bremen, Germany.

Asexual propagation by tissue culture in a laboratory in Bremen, Germany has been used to increase the number of plants for evaluation and has demonstrated that the unique combination of characteristics as herein disclosed for the new Phalaenopsis Orchid are firmly fixed and are retained through successive generations of asexual reproduction.

SUMMARY OF THE INVENTION

The following traits have been repeatedly observed and are determined to be basic characteristics of new cultivar which in combination distinguish this Phalaenopsis Orchid as a new and distinct cultivar:

1. Yellow green-colored flowers with red purple-colored labellum.
2. Freely flowering habit.
3. Upright, freely branching and sturdy flowering stems.
4. Excellent postproduction longevity.

Plants of the new cultivar differ primarily from plants of the parent cultivars in flower color.

Plants of the new Phalaenopsis Orchid can be compared to plants of the cultivar Nopsya, disclosed in U.S. Plant Pat. No. 10,682. In side-side comparisons conducted in Bremen, Germany, plants of the new Phalaenopsis Orchid differed from plants of the cultivar Nopsya in the following characteristics:

1. Plants of the new Phalaenopsis Orchid had smaller and darker green-colored leaves than plants of the cultivar Nopsya.
2. Plants of the new Phalaenopsis Orchid were more freely flowering than plants of the cultivar Nopsya.
3. Plants of the new Phalaenopsis Orchid had larger inflorescences with more flowers per inflorescence than plants of the cultivar Nopsya.
4. Plants of the new Phalaenopsis Orchid had larger flowers than plants of the cultivar Nopsya.
5. Plants of the new Phalaenopsis Orchid and the cultivar Nopsya differed in flower color.

BRIEF DESCRIPTION OF THE PHOTOGRAPHS

Colors in the photographs may appear different from the color values that appear in the detailed botanical description which more accurately describe the new cultivar.

The photograph on first sheet comprises a side perspective view of a typical flowering plant of the new cultivar grown in a 12-cm container.

The photograph at the top of the second sheet is a close-up view of typical inflorescences of the new cultivar.

The photograph at the bottom of the second sheet is a close-up view of a typical flower of the new cultivar.

DETAILED BOTANICAL DESCRIPTION

Plants of the new cultivar have not been observed under all possible environmental conditions. The phenotype may vary significantly with variations in environment such as temperature and light intensity, without however, any change in genotype. In the following description, color references are made to The Royal Horticultural Society Colour Chart, 1995 Edition, except where general terms of ordinary dictionary significance are used.

Plants used for the aforementioned photographs and following detailed botanical description were 11 months old and grown in 12-cm containers in Bremen, Germany, in a glass-covered greenhouse with day temperatures about 23 to 26° C., night temperatures about 22 to 25° C., and light levels about 18,000 lux. The photographs and the detailed botanical description were taken during the winter.

Botanical classification: Phalaenopsis cultivar Exotic Moon.

Parentage:

*Female, or seed, parent.*—Unidentified proprietary selection of Phalaenopsis, not patented.

*Male, or pollen, parent.*—Unidentified proprietary selection of Phalaenopsis, not patented.

Propagation:

*Type.*—Asexual propagation by tissue culture.

*Time to initiate and elongate roots.*—Summer and winter: About 56 days at 25° C.

*Time to produce a fully rooted young plant.*—Summer: About 175 days at 25° C. Winter: About 189 days at 25° C.

*Root description.*—Very thick, fleshy, and greenish white in color.

Plant description:

*Form.*—Two-ranked leaves affixed to a short central stem (monopodial growth). Single flowers arranged on upright and sturdy flowering racemes.

*Plant height, soil level to top of foliar plane.*—About 18 to 23 cm.

*Plant height, soil level to top of inflorescences.*—About 55 to 60 cm.

*Plant diameter.*—About 40 to 45 cm.

*Foliage description.*—Leaves simple, opposite; sessile. Quantity per plant: About six. Length: About 16 to 21 cm. Width: About 6 to 6.5 cm. Shape: Elliptic, elongated. Apex: Obtuse and rounded to slightly retuse. Base: Cuneate. Margin: Entire. Aspect: Mostly flat and folded upward from the midrib. Texture, upper and lower surfaces: Leathery, thick, glabrous. Venation: Parallel; veins are sunken within the lamina. Color: Young and mature foliage, upper surface: 147A, slightly glossy. Young and mature foliage, lower surface: 146A. Veins, upper and lower surfaces: Same as lamina.

Flower description:

*Flower type and habit.*—Single zygomorphic flowers arranged in racemes; flowers roughly pentagonal in shape. Flowering stems, upright, freely branching and sturdy. Plants freely flowering; plants typically produce one to three branched flowering stems with at least 7 to 9 flowers each. Flowers not fragrant. Flowers persistent. Flowers facing mostly outward.

*Natural flowering season.*—From January to April in northern Germany. Plants begin flowering about nine months after planting.

*Post-production longevity.*—Plants of the new Phalaenopsis Orchid maintain good leaf and flower substance for about three to six months on the plant under interior environmental conditions. Cut flowers of the new Phalaenopsis Orchid maintain good substance for about three to four weeks.

*Inflorescence length.*—About 30 cm.

*Inflorescence diameter.*—About 12 to 13 cm.

*Flower diameter.*—About 8.5 cm.

*Flower depth.*—About 2 cm.

*Flower buds.*—Shape: Ovoid. Length: About 2 cm. Width: About 1 cm. Color: 145A.

*Petals.*—Quantity/type: Three per flower; lateral petals similar in size and shape; the lowermost petal, the labellum, is deeply three-lobed. Lateral petals: Length: About 3.8 cm. Diameter: About 4 cm. Shape: Broadly ovate. Apex: Rounded. Base: Attenuate; fused with the column. Margin: Entire. Texture, upper and lower surfaces: Velvety, silky; smooth. Color: When opening and fully opened, upper surface: 1D to 154D; towards the base, occasional red purple, 58B, speckles; color becoming closer to 2D with subsequent development. When opening and fully opened, lower surface: 1D to 154D. Labellum: Length, not flattened: About 2.7 cm. Diameter, not flattened: About 1.8 cm. Shape: Deeply three-lobed with two prominent callosities on the upper surface at the central junction of the lateral lobes and base of the midlobe. The lateral lobes fold upward about the column, the midlobe extends forward and is terminated by two twisted filiform appendages (about 2 mm in length) at the apex. Callosities length: About 5 mm. Callosities width: About 4 mm. Texture, upper and lower surfaces: Velvety, silky; smooth. Color: When opening, upper surface: Lateral lobes and midlobe: 59B with minute yellow, 12A, speckles. Callosities: 12A. Central area: Close to 155D with red purple, 59B, streaks and speckles. When opening, lower surface: Lateral lobes: Close to 155D; lateral margins, 59C. Midlobe: 155D with red purple, 59C, and yellow, 7B, streaks and speckles. Fully opened, upper surface: Lateral lobes and midlobe: 59B with minute yellow, 14B, speckles. Callosities: 14B. Central area: Close to 155D with red purple, 59B, streaks and speckles. Fully opened, lower surface: Lateral lobes: Close to 155D; lateral margins, 59C. Midlobe: 155D with red purple, 59C, and yellow, 7B, streaks and speckles.

*Sepals.*—Quantity: Three per flower. Length: About 4 cm. Diameter: About 2.5 cm. Shape: Elliptic to ovate. Apex: Rounded acute. Base: Attenuate; fused with the petals and column. Margin: Entire. Texture, upper and lower surfaces: Velvety; smooth. Color: When opening and fully opened, upper surface: 1D to 154D, with red purple, 59B, speckles towards the base of the lateral sepals. When opening and fully opened, lower surface: 1D to 154D.

*Peduncles.*—Length: About 35 to 40 cm. Diameter: About 5 mm. Aspect: Upright. Strength: Strong, sturdy. Texture: Smooth, glabrous. Color: 146A overlain with 187A.

*Pedicels.*—Length: About 3.2 cm. Diameter: About 3 mm. Aspect: About 35° from vertical. Strength: Strong. Texture: Smooth, glabrous. Color: 154D.

*Reproductive organs.*—Arrangement: Stamens and pistils fused into a column. Anthers with pollen grains united into pollinia. Stigma situated under the column and behind the pollinia. Ovary inferior with three carpels. Column: Length: About 9 mm. Diameter: About 5 mm. Color: 155B. Pollinia: Quantity of pollen masses: Two. Diameter: About 9 mm. Color: 23B. Stigma: Shape: Rounded, concave. Length: About 5 mm. Diameter: About 4.5 mm. Color: 155D. Ovary: Length: About 1.5 cm. Diameter: About 2.5 mm. Color: 155A.

*Seed/fruit.*—Seed and fruit production has not been observed.

Disease/pest resistance: Resistance to known pathogens and pests common to Phalaenopsis Orchids has not been observed on plants of the new cultivar grown under commercial greenhouse conditions.

Temperature tolerance: Plants of the new Phalaenopsis Orchid have been observed to be tolerant to temperatures from about 14 to 32° C.

It is claimed:

1. A new and distinct cultivar of Phalaenopsis plant named 'Exotic Moon', as illustrated and described.

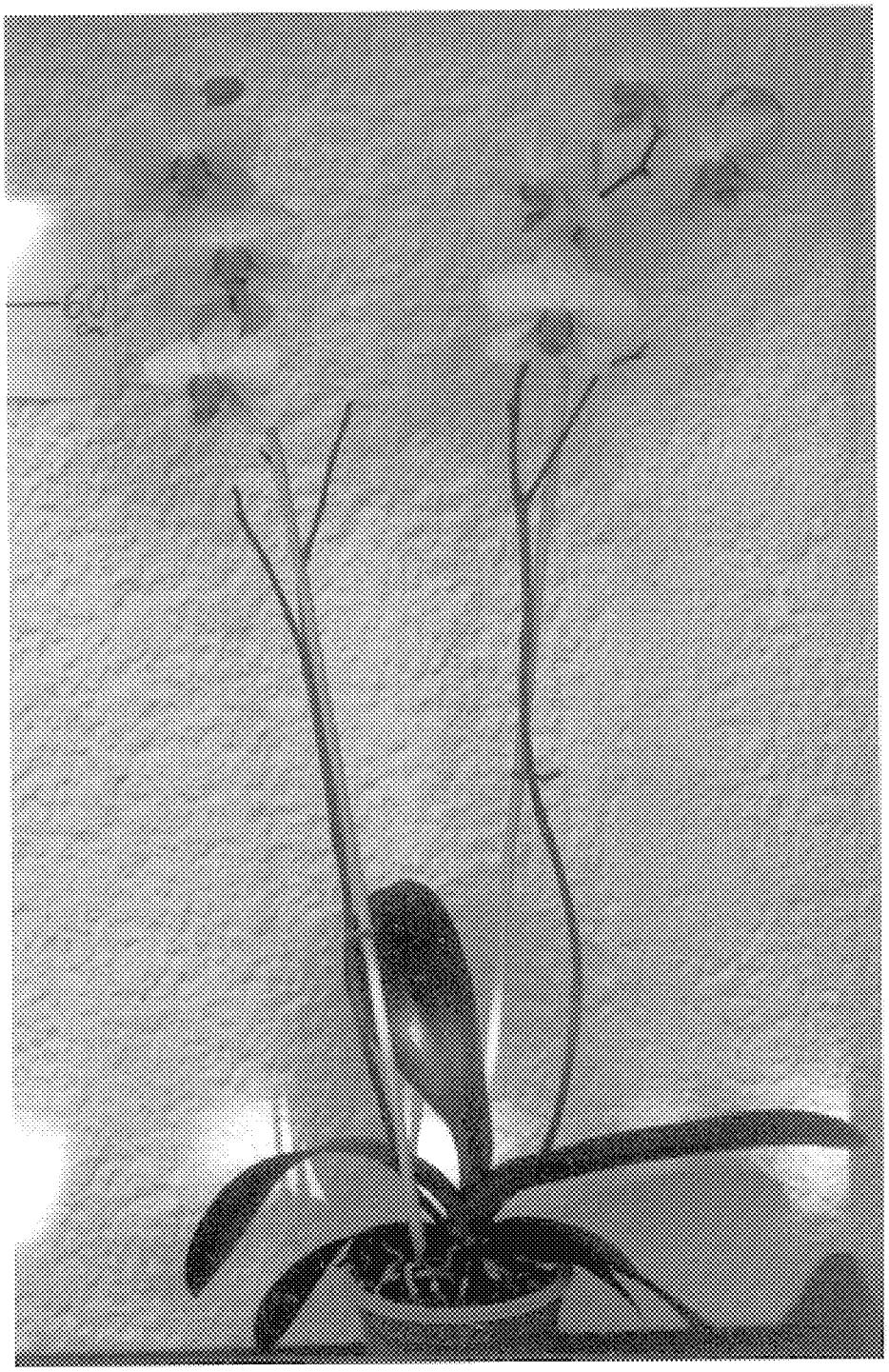

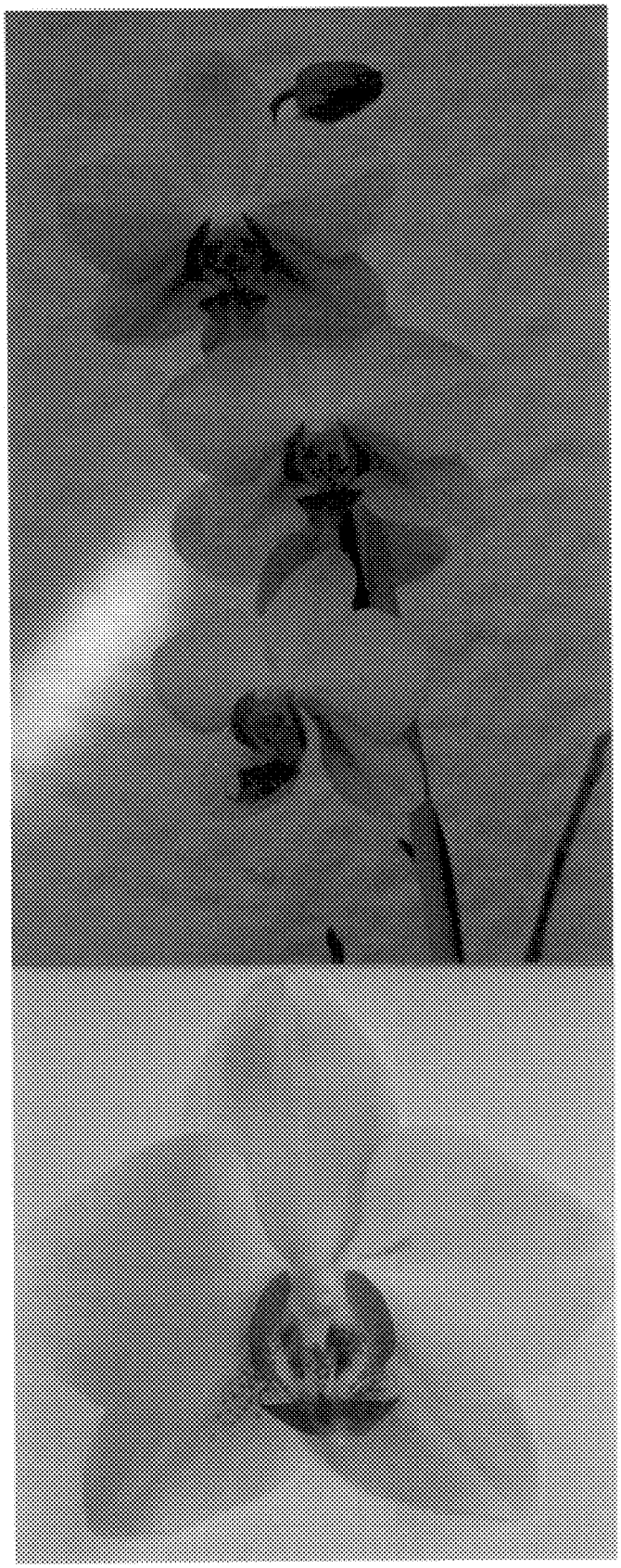

* * * * *